United States Patent
Borgmann et al.

(10) Patent No.: US 7,855,312 B2
(45) Date of Patent: Dec. 21, 2010

(54) METHOD FOR PROCESSING AN OLEFIN-CONTAINING PRODUCT STREAM

(75) Inventors: Wilfried Borgmann, Baierbrunn (DE); Josef Kunkel, Gauting (DE); Helmut Fritz, Munich (DE); Gerhard Lauermann, Bad Tolz (DE); Roland Walzl, Feldafing (DE); Klaus Muller, Kirchseeon (DE)

(73) Assignee: ExxonMobil Chemical Patents Inc., Houston, TX (US)

( * ) Notice: Subject to any disclaimer, the term of this patent is extended or adjusted under 35 U.S.C. 154(b) by 1265 days.

(21) Appl. No.: 10/508,983

(22) PCT Filed: Oct. 11, 2002

(86) PCT No.: PCT/EP02/11407

§ 371 (c)(1),
(2), (4) Date: Apr. 13, 2005

(87) PCT Pub. No.: WO03/033438

PCT Pub. Date: Apr. 24, 2003

(65) Prior Publication Data

US 2005/0222478 A1    Oct. 6, 2005

(30) Foreign Application Priority Data

Oct. 16, 2001    (DE) .............................. 101 50 480

(51) Int. Cl.
*C07C 1/00*    (2006.01)

(52) U.S. Cl. .................. 585/639; 585/638; 585/802; 585/809; 585/822; 585/833

(58) Field of Classification Search ............... 585/640, 585/809, 833, 638, 639, 802, 822
See application file for complete search history.

(56) References Cited

U.S. PATENT DOCUMENTS

| | | | |
|---|---|---|---|
| 4,387,263 A | 6/1983 | Vogt et al. | 585/640 |
| 4,547,602 A | 10/1985 | Tabak | 585/314 |
| 4,560,537 A | 12/1985 | Tabak | 422/190 |
| 6,303,841 B1 * | 10/2001 | Senetar et al. | 585/639 |

FOREIGN PATENT DOCUMENTS

EP    0 060 103    9/1982

\* cited by examiner

*Primary Examiner*—Prem C Singh
(74) *Attorney, Agent, or Firm*—Kevin M. Faulkner

(57) ABSTRACT

A method is described for processing an olefin-containing product stream (1) that contains, besides ethylene and propylene, longer-chain olefins and compounds of hydrocarbons with oxygen (oxygenates). Such a product stream (I) can occur in particular in olefin synthesis from methanol. The product stream is dewatered in successive process steps, optionally compressed in several steps and dried. Then it is subjected to fractionation. For removal of the undesired oxygenates it is proposed that the oxygenates be washed out of the gaseous product stream after the compression steps and before the drying step in a column (12) with methanol.

8 Claims, 1 Drawing Sheet

METHOD FOR PROCESSING AN OLEFIN-CONTAINING PRODUCT STREAM

This application claims benefit of the filing date of German Patent Application No. 101 50 480.2, filed Oct. 16, 2001.

FIELD OF THE INVENTION

This invention concerns a method for processing an olefin-containing product stream that contains, besides ethylene and propylene, longer chain olefins and compounds of hydrocarbons with oxygen (oxygenates), where the product stream is dewatered in successive process steps, optionally compressed in several steps and dried, and then sent to fractionation.

BACKGROUND OF THE INVENTION

Producing olefins from methanol have been considered an interesting alternative to the traditional production of olefins from petroleum. Methanol is considered to be a readily stored and managed intermediate product for utilization of hitherto unused natural gas. Thus, the increasing demands for olefins on the world market could also be served by using very cheap methane. For this reason, processes are being developed that produce short-chain olefins from methanol. Such processes operate, for example, catalytically according to the overall equation $2CH_3OH \rightarrow C_2H_4+2H_2O$. Besides the desired olefins, ethylene and propylene, longer-chain olefins and, especially, undesired compounds of hydrocarbons with oxygen (oxygenates) such as alcohols, ketones and organic acids also form. For this reason a costly secondary purification of the reaction product is necessary. One oxygenate that is particularly to be taken into account is dimethyl ether (DME), since it is one of the lightest oxygenates and behaves similarly to $C_3$ in distillation processes. Moreover, it is only slightly polar, so it can be difficult to remove by absorption. Accordingly, it would be beneficial to find additional methods to more easily remove oxygenates from olefins, particularly from an olefin stream synthesized from methanol U.S. Pat. Nos. 4,547,602 and 4,560,537 disclose a process for converting methanol to heavy hydrocarbons in the distillate range. In the first stage catalytic process, oxygenate is converted to lower olefins. The first stage effluent is cooled in an exchanger to condense water and a major amount of C5+ hydrocarbons. Byproduct water may be recovered from unreacted feedstock and discarded or a portion may be recycled.

U.S. Pat. No. 4,387,263 discloses a process for making C2 to C4 olefins from gas mixtures containing methanol, dimethyl ether. The reaction gasses, after condensation directs the reaction gasses and a condensed aqueous phase to a water scrubber in a water scrubbing column.

European Patent Application No. 0 060 103 discloses a process for converting methanol and/or dimethyl ether to a product containing ethylene. The product is condensed to form three phases—a liquid aqueous phase, a gaseous hydrocarbon phase and a liquid hydrocarbon phase. The liquid aqueous phase contains unreacted methanol and dimethyl ether. The liquid aqueous phase is stripped with low pressure steam to volatilize the methanol and/or dimethyl ether to from the aqueous phase. The methanol and/or dimethyl ether are recycled back to the reactor. Additionally, the gaseous hydrocarbon phase is contacted with methanol to selectively sorb unreacted dimethyl ether. An alternative contacts the gaseous phase with water to selectively remove dimethyl ether.

SUMMARY OF THE INVENTION

This invention provides a process for producing olefins from methanol such that oxygenate contaminants can be more easily removed from the olefin product. In one embodiment, the invention comprises a method for processing an olefin stream containing oxygenates (comprising organic compounds that contain at least one oxygen) and water. The method comprises providing an olefin stream containing oxygenates and water. The olefin stream is dewatered, and the dewatered olefin stream compressed. The compressed olefin stream is then washed with methanol to remove at least a portion of the oxygenate from the olefin stream. Following methanol wash, the olefin stream is contacted with water, and the water contacted olefin stream is fractionated.

In another embodiment, the water contacted olefin stream is dried prior to fractionating. In yet another embodiment, the washing of the olefin stream with the methanol and the water is carried out in a single wash column.

The invention also provides an embodiment, wherein the dewatered olefin stream is compressed to form a condensate containing dissolved heavy oxygenates and a gaseous olefin stream which is washed with the methanol. Desirably, the condensate is sent to a stripping column in which an overhead product of light hydrocarbons and a bottom product of $C_5+$ hydrocarbons and heavy oxygenates are obtained. Preferably, the overhead product of light hydrocarbons is sent to at least one compression step.

In one embodiment, there is a method for producing olefins from methanol. According to the method, a molecular sieve catalyst is contacted with a first amount of methanol to produce an olefin stream. The olefin stream comprises an oxygenate. The oxygenate comprises an organic compound that contains at least one oxygen. The olefin stream is dewatered. The dewatered olefin stream is compressed. Then, the olefin stream is washed with a second amount of methanol to remove at least a portion of the oxygenate from the olefin stream. The second amount is from 1% to 10% of the first amount. Next, the methanol washed olefin stream is contacted with water. Thereafter, the water contacted olefin stream is fractionated.

In another embodiment, the step of contacting a molecular sieve catalyst with a first amount of methanol occurs at a gas superficial velocity greater than 1 m/s. In another embodiment, the step of contacting converts from 90 wt. % to 98 wt. % of the first amount of methanol. In still another embodiment, the step of contacting converts above 98 wt. % to less than 100 wt. % of the first amount of methanol.

BRIEF DESCRIPTION OF THE DRAWING

The attached FIGURE shows an example of but one type of flow scheme of the invention in which methanol is used to remove undesirable oxygenates from an olefin stream synthesized from methanol.

DETAILED DESCRIPTION OF THE INVENTION

Figure 1:
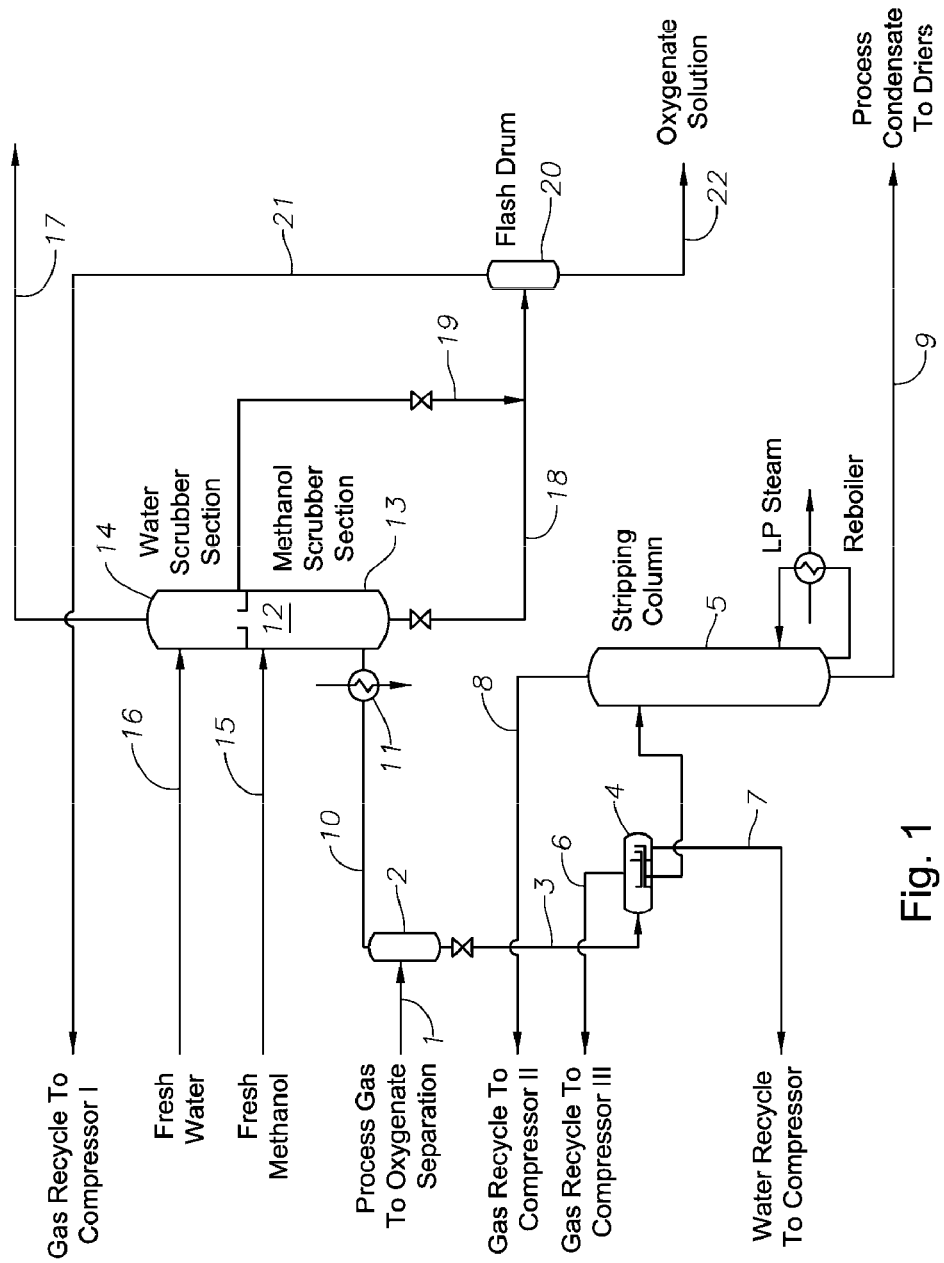

This invention provides a method for efficiently removing undesirable oxygenates from an olefin stream, particularly an olefin stream synthesized from methanol. The method is achieved in an economical way.

According to the invention, oxygenates are washed out of the gaseous olefin product stream after at least one compression step, and before the olefin product is dried. The oxygenates are washed out in a wash column with methanol.

The invention is based on the fact that the drying steps that are called for in conventional ethylene plants are not capable of handling more than very small amounts of oxygenates like aldehydes and ketones. Moreover, such oxygenates can polymerize under certain conditions, and the polymerization reactions can reduce the active surfaces of conventional drying schemes very rapidly. At present, there are no known dryers that are suitable for handling such components. For this reason, the oxygenates have to be removed from the product stream before they enter the cold part of the processing plant, which consists of olefin drying and fractionation.

One conceivable possibility for removing the oxygenates would be to use all of the fresh methanol that is provided for olefin synthesis to wash the oxygenates out of the olefin product stream before the olefin synthesis. However, this would result in the olefin synthesis being loaded with reaction products from the olefin synthesis. This can lead to the accumulation of undesirable components.

In this invention, the olefin stream containing the oxygenate contaminants is quenched (dewatered), compressed and dried before fractionation. The oxygenate removal step is desirably performed after at least one compression step. If multiple compression steps are used, it is desirable that the oxygenate removal step be performed between the third and fourth compression step. It is also desired that the oxygenate removal step be performed after compression and before drying.

According to the invention, a wash column is provided for removing the oxygenate contaminant. Desirably, the oxygenates are washed out of the gaseous product stream with methanol in the wash column. Only a relatively small amount of methanol is needed for the oxygenate removal. For example, 1% to 10%, preferably 3% of the total amount of methanol used in the olefin synthesis, is used to wash out the oxygenates to an acceptable limit.

In another embodiment of the invention, overhead gas accumulating in the methanol wash is further washed with water. This removes methanol that may become entrained in the olefin stream as a result of evaporation in the preceding methanol wash. The gaseous product stream that is recovered from this water wash contains, besides the olefins, only traces of oxygenates and methanol. The water washed olefin product stream is then sent to drying and fractionation.

In yet another embodiment of the invention, the water wash is carried out in an additional section of the wash column provided for the methanol wash. Desirably, a single wash column is provided for this, with the methanol wash being carried out in the lower part of the wash column, and the water wash in the upper part.

Another embodiment of the invention provides that the outlet pressure of at least one of the compression steps be adjusted so that, optionally after cooling, a hydrocarbon-containing condensate in which heavy oxygenates are dissolved is formed in addition to the gaseous product stream. The condensate can be sent to a stripping column, in which an overhead product of light hydrocarbons and a bottom product of $C_5+$ hydrocarbons and heavy oxygenates is obtained. The overhead product of light hydrocarbons is desirably sent to at least one compression step. The bottom product of heavy hydrocarbons and oxygenates can be sent to further processing.

The invention provides an economical method for removing oxygenates from an olefin-containing product stream, and enables effective oxygen separation at very low investment cost. The invention is also advantageous in that only a very small amount of methanol is needed to remove the oxygenates from the olefin stream and that the wash stream can be used as feed to the olefin synthesis reactor. The olefin synthesis reaction will not be adversely affected by the methanol wash containing absorbed oxygenate. Nearly the same amount of fresh methanol is available for olefin synthesis. Desirably, the amount of methanol used in the methanol wash will be 1% to 10% of the total amount of the methanol that is used in the olefin synthesis reaction.

In one embodiment of the invention, the olefin product is obtained by contacting methanol with an olefin forming catalyst in a reactor. Preferably, the catalyst is a molecular sieve catalyst.

Although the use of methanol to produce the olefin stream is preferred, other oxygenate components can be used as a feed. Such oxygenates comprise at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol includes an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$-$C_{20}$ alcohols; methyl ethyl ether; dimethyl ether; diethyl ether, di-isopropyl ether; formaldehyde; dimethyl carbonate; dimethyl ketone; acetic acid; and mixtures thereof. Dimethyl ether, or a mixture of dimethyl ether and methanol, are also preferred feeds.

Molecular sieves capable of converting an oxygenate such as methanol to an olefin compound include zeolites as well as non-zeolites, and are of the large, medium or small pore type. Small pore molecular sieves are preferred in one embodiment of this invention, however. As defined herein, small pore molecular sieves have a pore size of less than 50 nm (5.0 angstroms). Generally, suitable catalysts have a pore size ranging from 35 nm (3.5 angstroms) to 50 nm (5.0 angstroms), preferably from 40 nm (4.0 angstroms) to 50 nm (5.0 angstroms), and most preferably from 43 nm (4.3 angstroms) to 50 nm (5.0 angstroms).

Zeolite materials, both natural and synthetic, have been demonstrated to have catalytic properties for various types of hydrocarbon conversion processes. In addition, zeolite materials have been used as adsorbents, catalyst carriers for various types of hydrocarbon conversion processes, and other applications. Zeolites are complex crystalline aluminosilicates which form a network of $AlO_2^-$ and $SiO_2$ tetrahedra linked by shared oxygen atoms. The negativity of the tetrahedra is balanced by the inclusion of cations such as alkali or alkaline earth metal ions. In the manufacture of some zeolites, non-metallic cations, such as tetramethylammonium (TMA) or tetrapropylammonium (TPA), are present during synthesis. The interstitial spaces or channels formed by the crystalline network enable zeolites to be used as molecular sieves in separation processes, as catalyst for chemical reactions, and as catalyst carriers in a wide variety of hydrocarbon conversion processes.

Zeolites include materials containing silica and optionally alumina, and materials in which the silica and alumina portions have been replaced in whole or in part with other oxides. For example, germanium oxide, tin oxide, and mixtures thereof can replace the silica portion. Boron oxide, iron oxide, gallium oxide, indium oxide, and mixtures thereof can replace the alumina portion. Unless otherwise specified, the terms "zeolite" and "zeolite material" as used herein, shall mean not only materials containing silicon atoms and, optionally, aluminum atoms in the crystalline lattice structure thereof, but also materials which contain suitable replacement atoms for such silicon and aluminum atoms.

One type of olefin forming catalyst capable of producing large quantities of ethylene and propylene is a silicoaluminophosphate (SAPO) molecular sieve. Silicoaluminophosphate molecular sieves are generally classified as being microporous materials having 8, 10, or 12 membered ring structures. These ring structures can have an average pore size ranging from 35 nm (3.5 angstroms) to 150 nm (15 angstroms). Preferred are the small pore SAPO molecular sieves having an average pore size of less than 50 nm (5 angstroms), preferably an average pore size ranging from 35 nm (3.5 angstroms) to 50 nm (5 angstroms), more preferably from 35 nm (3.5 angstroms) to 42 nm (4.2 angstroms). These pore sizes are typical of molecular sieves having 8 membered rings.

According to one embodiment, substituted SAPOs can also be used in oxygenate to olefin reaction processes. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a [MeO$_2$] tetrahedral unit. The [MeO$_2$] tetrahedral unit carries a net electric charge depending on the valence state of the metal substituent. When the metal component has a valence state of +2, +3, +4, +5, or +6, the net electric charge is between -2 and +2. Incorporation of the metal component is typically accomplished adding the metal component during synthesis of the molecular sieve. However, post-synthesis ion exchange can also be used. In post synthesis exchange, the metal component will introduce cations into ion-exchange positions at an open surface of the molecular sieve, not into the framework itself.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferred are SAPO-18, SAPO-34, SAPO-35, SAPO-44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

An aluminophosphate (ALPO) molecular sieve can also be included in the catalyst composition. Aluminophosphate molecular sieves are crystalline microporous oxides which can have an AlPO$_4$ framework. They can have additional elements within the framework, typically have uniform pore dimensions ranging from 30 nm (3 angstroms) to 100 nm (10 angstroms), and are capable of making size selective separations of molecular species. More than two dozen structure types have been reported, including zeolite topological analogues. A more detailed description of the background and synthesis of aluminophosphates is found in U.S. Pat. No. 4,310,440, which is incorporated herein by reference in its entirety. Preferred ALPO structures are ALPO-5, ALPO-11, ALPO-18, ALPO-31, ALPO-34, ALPO-36, ALPO-37, and ALPO-46.

The ALPOs can also include a metal substituent in its framework. Preferably, the metal is selected from the group consisting of magnesium, manganese, zinc, cobalt, and mixtures thereof. These materials preferably exhibit adsorption, ion-exchange and/or catalytic properties similar to aluminosilicate, aluminophosphate and silica aluminophosphate molecular sieve compositions. Members of this class and their preparation are described in U.S. Pat. No. 4,567,029.

The metal containing ALPOs have a three-dimensional microporous crystal framework structure of MO$_2$, AlO$_2$ and PO$_2$ tetrahedral units. These as manufactured structures (which contain template prior to calcination) can be represented by empirical chemical composition, on an anhydrous basis, as:

mR: (M$_x$Al$_y$P$_z$)O$_2$

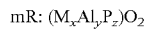

wherein "R" represents at least one organic templating agent present in the intracrystalline pore system; "m" represents the moles of "R" present per mole of (M$_x$Al$_y$P$_z$)O$_2$ and has a value of from zero to 0.3, the maximum value in each case depending upon the molecular dimensions of the templating agent and the available void volume of the pore system of the particular metal aluminophosphate involved, "x", "y", and "z" represent the mole fractions of the metal "M", (i.e. magnesium, manganese, zinc and cobalt), aluminum and phosphorus, respectively, present as tetrahedral oxides.

The metal containing ALPOs are sometimes referred to by the acronym as MeAPO. Also in those cases where the metal "Me" in the composition is magnesium, the acronym MAPO is applied to the composition. Similarly ZAPO, MnAPO and CoAPO are applied to the compositions which contain zinc, manganese and cobalt respectively. To identify the various structural species which make up each of the subgeneric classes MAPO, ZAPO, CoAPO and MnAPO, each species is assigned a number and is identified, for example, as ZAPO-5, MAPO-11, CoAPO-34 and so forth.

The silicoaluminophosphate molecular sieve is typically admixed (i.e., blended) with other materials. When blended, the resulting composition is typically referred to as a SAPO catalyst, with the catalyst comprising the SAPO molecular sieve.

Materials which can be blended with the molecular sieve can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, quartz, silica or silica or silica sol, and mixtures thereof. These components are also effective in reducing, inter alia, overall catalyst cost, acting as a thermal sink to assist in heat shielding the catalyst during regeneration, densifying the catalyst and increasing catalyst strength. It is particularly desirable that the inert materials that are used in the catalyst to act as a thermal sink have a heat capacity of from 0.05 to 1 cal/g-° C., more preferably from 0.1 to 0.8 cal/g-° C., most preferably from 0.1 to 0.5 cal/g-° C.

Additional molecular sieve materials can be included as a part of the SAPO catalyst composition or they can be used as separate molecular sieve catalysts in admixture with the SAPO catalyst if desired. Structural types of small pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. Structural types of medium pore molecular sieves that are suitable for use in this invention include MFI, MEL, MTW, EUO, MIT, HEU, FER, AFO, AEL, TON, and substituted forms thereof. These small and medium pore molecular sieves are described in greater detail in the *Atlas of Zeolite Structural Types*, W. M. Meier and D. H. Olsen, Butterworth Heineman, 3rd ed., 1997, the detailed description of which is explicitly incorporated herein by reference. Preferred molecular sieves which can be combined with a silicoaluminophosphate catalyst include ZSM-5, ZSM-34, erionite, and chabazite.

The catalyst composition, according to an embodiment, preferably comprises from 1% to 99%, more preferably from 5% to 90%, and most preferably from 10% to 80%, by weight of molecular sieve. It is also preferred that the catalyst composition have a particle size of from 0.2 µm (20 angstroms) to 30 µm (3,000 angstroms), more preferably from 0.3 µm (30 angstroms) to 2 µm (200 angstroms), most preferably from 0.5 µm (50 angstroms) to 1.5 µm (150 angstroms).

The catalyst can be subjected to a variety of treatments to achieve the desired physical and chemical characteristics. Such treatments include, but are not necessarily limited to hydrothermal treatment, calcination, acid treatment, base treatment, milling, ball milling, grinding, spray drying, and combinations thereof.

A molecular sieve catalyst particularly useful in making ethylene and propylene is a catalyst which contains a combination of SAPO-34, and SAPO-18 or ALPO-18 molecular sieve. In a particular embodiment, the molecular sieve is a crystalline intergrowth of SAPO-34, and SAPO-18 or ALPO-18.

To convert methanol or other oxygenate to olefin, conventional reactor systems can be used, including fixed bed, fluid bed or moving bed systems. Preferred reactors of one embodiment are co-current riser reactors and short contact time, countercurrent free-fall reactors. Desirably, the reactor is one in which an oxygenate feedstock can be contacted with a molecular sieve catalyst at a weight hourly space velocity (WHSV) of at least 1 $h^{-1}$, preferably in the range of from 1 $hr^{-1}$ to 1000 $hr^{-1}$, more preferably in the range of from 20 $hr^{-1}$ to 1000 $hr^{-1}$, and most preferably in the range of from 50 $hr^{-1}$ to 500 $hr^{-1}$. WHSV is defined herein as the weight of oxygenate, and reactive hydrocarbon which may optionally be in the feed, per hour per weight of the molecular sieve in the reactor. Because the catalyst or the feedstock may contain other materials which act as inerts or diluents, the WHSV is calculated on the weight basis of the oxygenate feed, and any reactive hydrocarbon which may be present with the oxygenate feed, and the molecular sieve contained in the reactor.

Preferably, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The process can generally be carried out at a wide range of temperatures. An effective operating temperature range can be from 200° C. to 700° C., preferably from 300° C. to 600° C., more preferably from 350° C. to 550° C. At the lower end of the temperature range, the formation of the desired olefin products may become markedly slow with a relatively high content of oxygenated olefin by-products being found in the olefin product. However, the selectivity to ethylene and propylene at reduced temperatures may be increased. At the upper end of the temperature range, the process may not form an optimum amount of ethylene and propylene product, but the conversion of oxygenate feed will generally be high.

Operating pressure also may vary over a wide range, including autogenous pressures. Effective pressures include, but are not necessarily limited to, a total pressure of at least 1 psia (7 kPa), preferably at least 5 psia (34 kPa). The process is particularly effective at higher total pressures, including a total pressure of at least 20 psia (138 kPa). Preferably, the total pressure is at least 25 psia (172 kPa), more preferably at least 30 psia (207 kPa). For practical design purposes it is desirable to use methanol as the primary oxygenate feed component, and operate the reactor at a pressure of not greater than 500 psia (3445 kPa), preferably not greater than 400 psia (2756 kPa), most preferably not greater than 300 psia (2067 kPa).

Undesirable by-products can be avoided by operating at an appropriate gas superficial velocity. As the gas superficial velocity increases the conversion decreases avoiding undesirable by-products. As used herein, the term, "gas superficial velocity" is defined as the combined volumetric flow rate of vaporized feedstock, which includes diluent when present in the feedstock, as well as conversion products, divided by the cross-sectional area of the reaction zone. Because the oxygenate is converted to a product having significant quantities of ethylene and propylene while flowing through the reaction zone, the gas superficial velocity may vary at different locations within the reaction zone. The degree of variation depends on the total number of moles of gas present and the cross section of a particular location in the reaction zone, temperature, pressure and other relevant reaction parameters.

In one embodiment, the gas superficial velocity is maintained at a rate of greater than 1 meter per second (m/s) at least one point in the reaction zone. In another embodiment, it is desirable that the gas superficial velocity is greater than 2 m/s at least one point in the reaction zone. More desirably, the gas superficial velocity is greater than 2.5 m/s at least one point in the reaction zone. Even more desirably, the gas superficial velocity is greater than 4 m/s at least one point in the reaction zone. Most desirably, the gas superficial velocity is greater than 8 m/s at least one point in the reaction zone.

According to yet another embodiment of the invention, the gas superficial velocity is maintained relatively constant in the reaction zone such that the gas superficial velocity is maintained at a rate greater than 1 m/s at all points in the reaction zone. It is also desirable that the gas superficial velocity be greater than 2 m/s at all points in the reaction zone. More desirably, the gas superficial velocity is greater than 2.5 m/s at all points in the reaction zone. Even more desirably, the gas superficial velocity is greater than 4 m/s at all points in the reaction zone. Most desirably, the gas superficial velocity is greater than 8 m/s at all points in the reaction zone.

The amount of ethylene and propylene produced in the oxygenate to olefin process can be increased by reducing the conversion of the oxygenates in the oxygenate to olefins reaction. However, reducing the conversion of feed oxygenates in the oxygenate conversion reaction tends to increase the amount of oxygenated hydrocarbons, particularly including dimethyl ether, that are present in the olefin product. Thus, control of the conversion of feed to the oxygenate reaction process can be important.

According to one embodiment, the conversion of the primary oxygenate, e.g., methanol, is from 90 wt % to 98 wt %. According to another embodiment the conversion of methanol is from 92 wt % to 98 wt %, preferably from 94 wt % to 98 wt %.

According to another embodiment, the conversion of methanol is above 98 wt % to less than 100 wt %. According to another embodiment, the conversion of methanol is from 98.1 wt % to less than 100 wt %; preferably from 98.2 wt % to 99.8 wt %. According to another embodiment, the conversion of methanol is from 98.2 wt % to less than 99.5 wt; preferably from 98.2 wt % to 99 wt %.

In this invention, weight percent conversion is calculated on a water free basis unless otherwise specified. Weight percent conversion on a water free basis is calculated as: 100× (weight oxygenate fed on a water free basis–weight oxygenated hydrocarbon in the product on a water free basis). The water free basis of oxygenate is calculated by subtracting out the water portion of the oxygenate in the feed and product, and excluding water formed in the product. For example, the weight flow rate of methanol on an oxygenate free basis is calculated by multiplying the weight flow rate of methanol by 14/32 to remove the water component of the methanol. As another example, the rate flow rate of dimethyl ether on an oxygenate free basis is calculated by multiplying the weight flow rate of dimethylether by 28/46 to remove the water component of the dimethyl ether. If there is a mixture of oxygenates in the feed or product, trace oxygenates are not included. When methanol and/or dimethyl ether is used as the feed, only methanol and dimethyl ether are used to calculate conversion on a water free basis.

In this invention, selectivity is also calculated on a water free basis unless otherwise specified. Selectivity is calculated as: 100×wt % component/(100−wt % water−wt % methanol−wt % dimethyl ether) when methanol and/or dimethyl ether is used as the feed.

An example of the invention is shown in the Figure. According to the Figure, an olefin product stream containing, in addition to ethylene and propylene, longer chain olefins and oxygenates, is sent from a reactor for production of olefins from methanol (not shown in the figure) via a pipe 1 to a gas-liquid separation device 2. Condensate, which accumulates in the gas-liquid separation device 2, and contains small amounts of hydrocarbons, is sent via a pipe 3 to a three-phase separator 4. Gas and water that accumulate in the three-phase separator are sent back to gas compressors via pipes 6 and 7. A large quantity of heavy oxygenates is dissolved in the remaining hydrocarbon-containing condensate. This condensate is sent to a stripping column 5.

Overhead gas that forms in the stripping column 5 is sent to gas compressors via a pipe 8. Heavy $C_5+$ hydrocarbons in which heavy oxygenates are dissolved are removed as bottom product via a pipe 9. This bottom by-product stream can be sent to further processing.

The olefin product stream in the gas-liquid separation device 2 is sent via a pipe 10 to the bottom portion of a wash column 12, after slight heating by means of heat exchanger 11. The oxygenates are washed out of the olefin product stream in a lower part 13 of the wash column 12 using fresh methanol. The fresh methanol is sent to the wash column 12 via a pipe 15.

Overhead gas from the methanol wash is sent to an additional wash, for which an upper part 14 of the wash column is provided. There, the overhead gas, which can contain evaporated methanol from the methanol wash is contacted with fresh water, which is sent to the wash column 12 via a pipe 16. The overhead gas exiting the upper part 14 of the wash column 12 contains only tolerable traces of oxygenates and methanol.

The overhead gas exiting the upper part 14 is sent via a pipe 17. This gas can be sent, for example, to an alkali wash and to a drying step. Then fractionation of the olefin (not shown in the Figure) is carried out.

The bottom product of the water wash is sent partly through the lower part 13 of the wash column 12, and partly to a flash drum 20 as by-pass via a pipe 19. The gas accumulating in flash drum 20 contains predominantly ethylene and propylene, and is sent back to the process via the compression steps. The liquid accumulating in flash drum 20 is a methanol-water solution that contains the oxygenates in a high concentration. This liquid is removed via a pipe 22, and can be sent to incineration or otherwise utilized. Alternatively, this solution can be sent to a methanol-water distillation separation, where the oxygenates remain in the distillate. The solution can also be returned to the process together with the methanol. Through other separation steps, it is also possible to obtain clean methanol and to discard the oxygenate. In the case of a light waste gas, it may be meaningful to choose the pressure in pipe 1 after the compression steps so that no hydrocarbon condensate accumulates. In this case, the three-phase separator 4 and the stripping column 5 can be omitted.

What is claimed is:

1. A method for producing olefins from methanol, the method comprising the steps of:
   contacting a molecular sieve catalyst with a first amount of methanol to produce an olefin stream, comprising an oxygenate wherein the oxygenate comprises an organic compound that contains at least one oxygen;
   removing oxygenates from the olefin stream by the steps consisting of:
   dewatering the olefin stream;
   compressing the dewatered olefin stream one or more times;
   washing the dewatered olefin stream with a second amount of methanol to remove at least a portion of the oxygenate from the olefin stream, wherein the second amount is from 1% to 10% of the first amount;
   contacting the methanol washed olefin stream with water;
   drying the water contacted olefin stream; and
   fractionating the dried olefin stream to produce an olefin stream.

2. The method of claim 1, wherein the washing the olefin stream with methanol to remove at least a portion of the oxygenate from the olefin stream; and the contacting the methanol washed olefin stream with water is carried out in a single wash column.

3. The method of claim 1, wherein the dewatered olefin stream is compressed to form a condensate containing dissolved heavy oxygenates and a gaseous olefin stream which is washed with the methanol.

4. The method of claim 3, further comprising sending the condensate to a stripping column in which an overhead product of light hydrocarbons and a bottom product of $C_5+$ hydrocarbons and heavy oxygenates are obtained.

5. The method of claim 4, wherein the overhead product of light hydrocarbons is sent to at least one compression step.

6. The process of claim 1, wherein the step of contacting the molecular sieve catalyst occurs at a gas superficial velocity greater than 1 m/s.

7. The process of claim 1, wherein the step of contacting the molecular sieve catalyst converts from 90 wt. % to 98 wt. % of the first amount of methanol.

8. The process of claim 1, wherein the step of contacting converts above 98 wt. % to less than 100 wt. % of the first amount of methanol.

* * * * *